Figure 1:
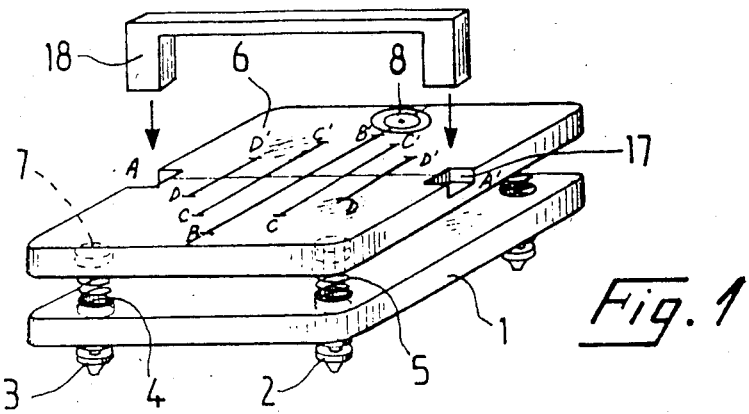

United States Patent [19]

Walthert

[11] Patent Number: 4,805,637
[45] Date of Patent: Feb. 21, 1989

[54] APPARATUS FOR THE DETECTION AND CORRECTION OF ANOMALIES IN THE EQUILIBRIUM OF THE HUMAN BODY

[76] Inventor: Nicole Walthert, 6, rue de Jargeau, F-45000 Orleans, France

[21] Appl. No.: 60,710

[22] PCT Filed: Sep. 24, 1986

[86] PCT No.: PCT/FR86/00325
§ 371 Date: May 20, 1987
§ 102(e) Date: May 20, 1987

[87] PCT Pub. No.: WO87/01923
PCT Pub. Date: Apr. 9, 1987

[30] Foreign Application Priority Data
Sep. 25, 1985 [FR] France .................... 85 14196

[51] Int. Cl.⁴ ............................................. A51B 5/10
[52] U.S. Cl. .................................. 128/774; 177/200; 73/65
[58] Field of Search ........................... 128/781, 774; 177/200 V; 73/65

[56] References Cited

U.S. PATENT DOCUMENTS 3,826,145 7/1974 McFarland .
4,492,236 1/1985 Pile ...................................... 128/781

FOREIGN PATENT DOCUMENTS 2094700 6/1970 France .
2443235 12/1978 France .
2472929 7/1981 France ............................. 128/774
2542991 3/1983 France .

OTHER PUBLICATIONS

French Search Report.

Primary Examiner—William E. Wayner
Attorney, Agent, or Firm—Armstrong, Nikaido, Marmelstein, Kubovcik

[57] ABSTRACT

A movable plate (6) which rests through springs (5) on a base (1) which itself bears on the ground by means of height adjustable supports (2,3) is provided with a spherical bubble level (8), with marks AA', BB', CC', DD', which define the positioning of the feet on said plate and with a removable setting system (18) with respect to the transversal line AA'. Application to the correction of equilibrium anomalies.

7 Claims, 2 Drawing Sheets

APPARATUS FOR THE DETECTION AND CORRECTION OF ANOMALIES IN THE EQUILIBRIUM OF THE HUMAN BODY

The invention relates to an apparatus for detecting and correcting anomalies in the equilibrium of the human body, based on the interpretation of the distribution of the weight of the body on the bearing points of the feet.

It is known that the center of gravity of the human body is situated at the level of the third lumbar vertebra which forms one of the most important points of the spinal column for maintaining equilibrium, at the same time as one of the most vulnerable for it supports all the weight above it whereas all the party of the body below it is suspended therefrom. This third lumbar vertebra is the seat of the most current lesions of the column, for in all the changes of posture due to the mobility and to the locomotion of the human body, the center of gravity tends to maintain a vertical line going from the top of the head to the center of the planter arch, that is to say that all the movements of the body pass through this vertebra. Thus, the slightest bone or muscular lesion results in an attempt to compensate in the sense of a normal vertical line between the feet and the head which will result in an imbalance and a poor distribution of the loads on the plantar arch.

It is known that the weight of the body in the upright and motionless position must be normally distributed over three bearing points of the plantar arch.

The plantar arch does not form an equilateral triangle but has three arches and three bearing points which form a comparable structure. The bearing points are included in the contact zone with the ground which receives the plantar impression and they correspond to the head of the first metatarsal, to the head of the fifth metatarsal and to the posterior tuberosities of the calcaneum. Each bearing point is common to two adjacent arches. The internal arch (calcaneum-head of the first metatarsal) has the scaphoid as ground, the external arch (calcaneum-head of the fifth metatarsal) has the large apophysis of the calcaneum as crown. The front arch (head of the first metatarsal, head of the fifth metatarsal) has as crown the head of the second metatarsal. The weight of the body is distributed half on the forefoot and half on the rear foot, in line with the extension of the front edge of the leg, which corresponds to the crowns of the internal and external arches, that is to say to the center of the instep.

The distribution of the bearing pressures on the ground is very important for attaining equilibrium. In fact, it is the bearing pressures perceived by the sole of the feet which inform the nervous system as a whole, including internal ear and cerebellum. By reflex movements all the muscles for maintaining verticality, for opposing gravity contract and equilibrium is attained.

As soon as a defect of bearing on the ground appears, so a defect of sensorial plantar information, that causes a nervous stimulation and muscular response defects which ends in imbalance or an unstable equilibrium. With the center of gravity displaced, compensation forces are exerted by the body causing deformations, pains, even giddiness and impaired coordination.

To overcome these disturbances, it then seems necessary, on the one hand, for the person to be conscious of and estimate the anomaly of equilibrium of his body, and on the other hand to be able to correct this anomaly by progressively rectifying this position until he arrives at as good a distribution of his weight as possible.

Apparatus exist which allow the user to visualise the distribution of his weight on each of his legs and which include essentially two mobile bearing surfaces, independent and having a connection device of the same kind as the linkages existing in weight scales, which translate on a scale the difference of weight applied to each of these surfaces. To these apparatus subsidiary devices are added, such as cross ruled mirrors by means of which the person may have the image of his body and himself rectify the disymmetry of his position.

A construction such as described in FR-A-2 443 235 is also known in which two stages of superimposed plates rest on the ground with interpositioning of dampers between each stage, the upper stage being formed of two independent plates on which the feet come to bear, each plate being associated with an inclination indicator.

Other systems allow poor weight distribution to be detected by examining impressions of feet marked to a greater or lesser extent on a support.

These devices have numerous drawbacks for they only give coarse indications of the imbalance of the body and the desired compensation can then only consist in rectifying the general verticality of the body which is far from being sufficient.

Moreover, known systems having several plates are complicated to construct, difficult to adjust and very delicate to operate by the user.

The invention brings a solution to this problem in that it provides an apparatus which allows not only poor distribution of the weight of a person on his two feet to be detected, but also an imbalance of distribution of the weight on the plantar arch, which apparatus is further extremely accurate, very simple to manufacture and use, which makes it particularly well adapted for arousing in numerous persons efficient correction reactions.

The apparatus of the invention includes a single mobile plate which rests, through at least three deformable members, on a base bearing on the ground and which includes an indicating member of the spirit level kind, integral with the movements of this latter, said mobile plate, further having elements marking the positioning of one or of both feet formed of axial lines along the axis of the feet, as well as a removable system for fixing the foot with respect to a transverse line dividing the weight of the body, in the middle of said plate. According to a particular feature of the invention, the removable fixing system is formed of a rigid half frame cooperating with notches provided on the plate at the ends of the transverse median line or of a resilient strip retained by said notches or else a comb cooperating with holes provided on the axial lines and the transverse lines.

Figures 2, 3:
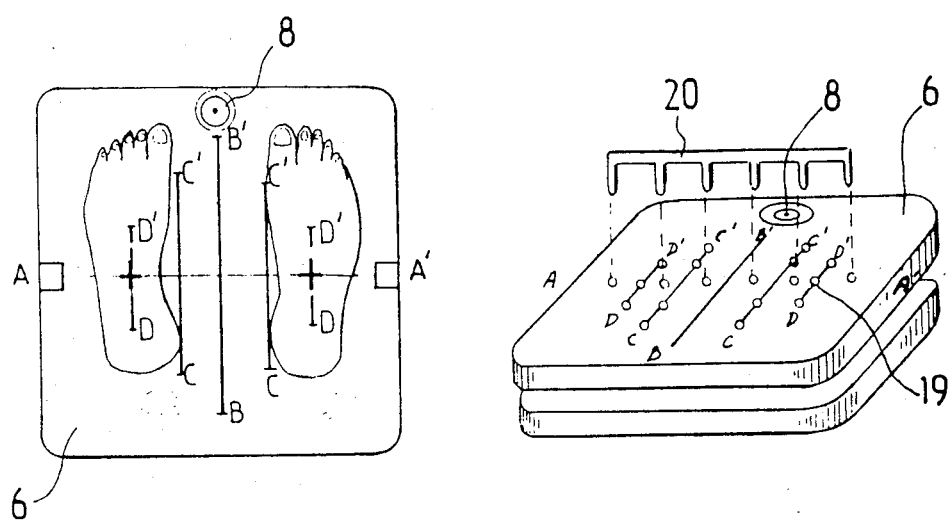
Figure 4:
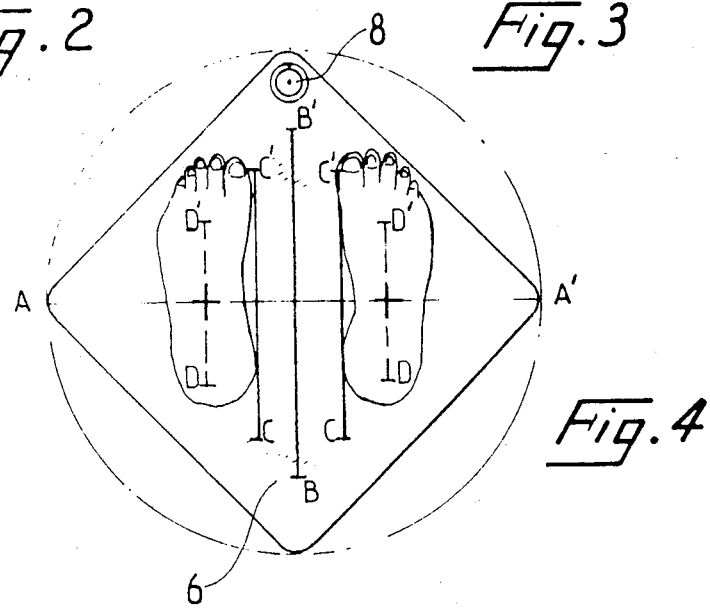
Figure 5:
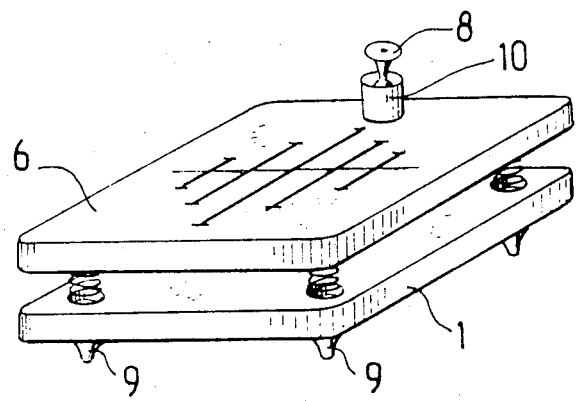
Figure 6:
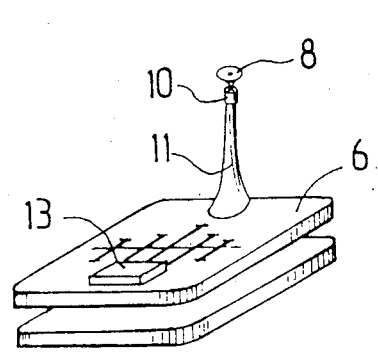
Figure 7:
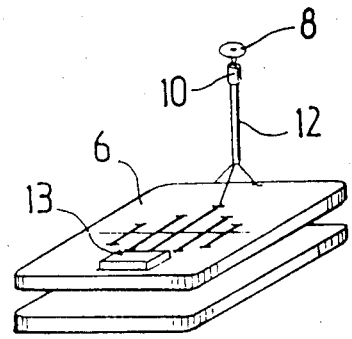
Figure 8:
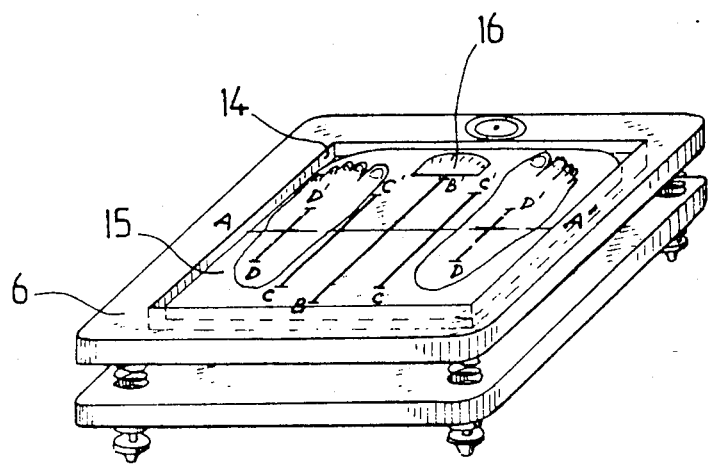

Other particular features and advantages of the invention will be clear from the description which follows of embodiments given by way of examples, and with reference to the accompanying drawings which show:

FIG. 1, a perspective view of the apparatus;

FIG. 2, a top view of the support plate showing bearing of the two feet;

FIG. 3, a perspective view of a variant of construction of the upper plate;

FIG. 4, a top view of a variant of construction of the support plate;

FIGS. 5 and 8 perspective views of a variant of construction of the apparatus and FIGS. 6 and 7 two schematical perspective views showing variants of fitting the spirit level.

The apparatus shown in FIG. 1 includes essentially a base 1 bearing on the ground through four supports adjustable in height by means of a wheel 3. The base is provided at its four corners, in line with the feet, with four recesses 4 serving as housing for springs 5. These springs, made advantageously from steel, are of equal height, of equal calibration and sufficiently resistant to crushing to prevent the plate from abutting against base 1 when it supports its load. An upper plate 6 of a size similar to that of the base rests by its four corners on springs 5. It is also provided with recesses 7 in which said springs are positioned. At the upper part of the plate is set a spherical spirit level 8 possibly covered with a magnifying lens. Plate 6 is made from a rigid and undeformable material such as a plywood, a plastic material or a fairly thick metal sheet.

The apparatus includes on its upper plate a transverse line AA' and an axial line BB' in accordance with the axis of the feet at the end of which is situated a spirit level 8, the two lines being the medians of the square formed by plate 6. Other lines CC' and DD' parallel to the lines BB' are disposed symmetrically on each side of this latter, with even spacing, the outer lines DD' being substantially at equal distances from the edge of the plate and from the axial line BB'. The user may thus place the internal edges of each foot along lines CC' or DD' so that the bearing force of his right foot and of his left foot are distributed symmetrically with respect to the axial line BB' as can be seen more precisely in FIG. 2.

In order to perfect the position of the feet on the apparatus, along the transverse line AA', true line of distribution of the weight of the body (half towards the front, half towards the rear), vertical notches 17, situated at each end of this line, will allow the passage of a system for fixing the feet formed preferably from a rigid material having the form of half of a frame 18 whose free edges slide in the notches or grooves 17. The free edges are sufficiently high to allow the feet to be fixed, even with high heeled shoes.

In a variant of construction not shown, frame 18 may be replaced by a resilient material, of a form similar to that of a strip, this strip would pass around the apparatus above and below, and would be retained in notches 17 so as to be perfectly superimposed on the transverse line AA'. The user would slide his feet under the resilient strip until the front edge of the leg is reached.

For correctly positioning the feet by means of the rigid frame 18, the feet are placed along lines CC' or DD', as mentioned above, and they are engaged under the frame until the front edge of the leg comes into abutment against the horizontal part of the frame. The center of the instep corresponding to the crowns of the internal and external arches of the bearing points of the body, is then centered on the points at which the transverse line AA' meets the axial lines CC' and DD' underlined by crosses + shown in FIG. 2. It is recommended by means of a pencil to mark the impression of each foot on the upper plate 6 so as to avoid fixing at each exercise. It is obvious that the fixing systems will be removed after the feet are correctly positioned on the apparatus.

Finally, and according to a variant illustrated in FIG. 3, for perfect positioning of the feet in the longitudinal direction and in the transverse direction, lines CC' and DD', parallel and equidistant from the large median line BB', may be pierced with small holes 19, in which will be placed the six teeth of a comb 20, the comb projecting from the surface of the plate and serving as a guide or setting for the internal edge of each foot. In so far as transverse fixing is concerned, the same system of holes in the transverse line allowing the use of the comb is possible. The holes may in all cases pass through the whole of the upper plate 6 through its thickness. If the apparatus is used while wearing shoes, the comb will be cleared by pulling it upwards until it comes into contact with the lower part of the front edge of the leg. In all cases, the fixing systems will be removed after the feet have been positioned and before use of the apparatus.

The apparatus is used for diagnosing and correcting upright imbalance, without moving, but also stopped movement equilibrium, such for example as equilibrium in a squatting position. Though the foot must remain strictly bearing on the upper plate through its three bearing points and not moved despite the changes of shape of the arches which tend to be crushed normally, the leg on the other hand changes orientation and any transverse fixing system left in position would be a hindrance to the squatting position. The invention is based on a perfect positioning of the feet on the apparatus. In fact, it is known that the vertical equilibrium of man on two feet or on one foot, corresponds to the fair distribution of his weight over the three bearing points of the plantar arch. With this invention, with the feet correctly positioned, and the spirit level previously adjusted by means of the adjustable supports, it is certain that when the bubble of the spirit level 8 remains centered, when in the upright or squatting position on the apparatus, the pressures of the plantar arch on the ground materialized here by the upper plate of the apparatus are correctly distributed.

FIG. 4 illustrates a variant of construction in which the plate is square, but the spirit level is located in a corner and the lines CC' and DD' are oriented as shown on each side of the axial line BB'. The outer form of plate 6 may also be circular as shown with a broken line.

Other variants of construction are illustrated in FIGS. 5 to 8.

In FIG. 5, base A bears on the ground through fixed feet 9. To compensate for the inherent flatness of the ground, the spirit level 8 is then mounted on an adjustment ball joint 10 which allows the bubble to be centered and consequently allows the unevenness of the ground to be counterbalanced before using the apparatus.

This ball joint mounting would also allow an upper plate to be used which is slanted with respect to the ground.

In the construction shown in FIGS. 6 and 7, spirit level 8 is fixed to a column 11 or to a rod 12 mounted on tripod and adjustable in height, both being fixed to plate 6. Each also has an adjustment ball joint 10. This arrangement brings the spirit level closer to the eye of the user. A counterweight 13 is moreover fixed to the plate for compensating for the weight of the column or the rod.

In the representation shown in FIG. 8, plate 6 is provided with a central recess 14 which serves as housing for a personal weighing machine 15 with its weight indicator 16. The weighing machine is centered so that the user may place his feet thereon in alignment of the axial line CC', DD' and AA'.

The apparatus thus described in its multiple variants is used in the following way, after the bubble of the spirit level 6 has been centered using the supports.

After positioning the feet along line CC' or DD' then with respect to the frame or comb fixing system, the position of the bubble is observed.

If the weight is distributed normally on the bearing points of the feet, the center of gravity of the body is in its right position and the bubble of spirit level 8 is perfectly centered. Any offsets of this bubble from the center corresponds to an imbalance of the body and to a poor distribution of the weight at the level of the foot. The user sees it visually and may himself, by muscular action, provide the correction of his anomaly of equilibrium by accentuating the pressure of one foot or of both towards the front or towards the rear so as to progressively bring the bubble back to its central point. The position of the bubble before correction informs the user about the orientation or the compensation which he must carry out. The apparatus thus allows the user to ensure the correction immediately after this diagnosis of the imbalance, for he has been conscious of the plantar perception which is an essential factor in maintaining equilibrium, which caused him an osteoarticular and muscular reaction. The repetition of these movements for centering the bubble lead the user progressively to eliminate the insufficiencies of some muscles by causing them to work so as to arrive at equilibrium of the body.

Thus, with this invention the transfers of weight at the level of the feet may be studied on floors of different slants and diagnosises may be made as to the bearing defects at the level of each bearing point of the plantar arch. The possibility which the invention offers is important in the practice of different sports where the transfers of bearing force are necessary and require fine coordination: for example skis, surfboards, surfing, golfing . . . etc.

The exercises, whether they are on a flat ground, with the bubble of the spirit level centered on the plate parallel to the ground, or with the bubble of the spirit level centered on a slanted ground, by raising one or both feet from the apparatus, always put the center of gravity of the body in its place. The exercises may be crouching exercises where all the body comes into play in the search for equilibrium. But they may also be exercises which leave the upper part of the body fixed from the center of gravity and mobilize the lower part of the body or conversely. After use the user feels a correct confortable bearing force which is called balance on the ground. He holds himself better vertically, walks better and keeps his stabilizing musculature correctly in all his movements from information acquired during use of the apparatus. Daily upkeep and the execution of different exercises of short duration on the apparatus is sufficient for correcting the right posture, for correcting current deformations, for giving correct tonicity back to all the equilibrium muscles, so for giving the body again equilibrium and flexibility coordination.

Thus, this invention allows the imbalances to be studied under numerous conditions and bearing force imperfections to be detected at the same time as the unsatisfactory muscular responses and allows them to be corrected. With this invention, all the muscular chains of the posture may be studied. The nervous system being the link between the bearing force on the ground and the muscular response of equilibrium, it will be readily understood that this apparatus will find numerous applications in neurology.

The invention has been described with reference to certain embodiments of the apparatus shown in FIGS. 1 to 8. Other embodiments not shown also form part of the invention. Similarly certain constituent parts of the apparatus may be modified without departing from the scope of the invention.

Thus, the spirit level used could be a pendulum whose movements will be detected and transmitted electrically, for example through resistors or electric contactors associated with light indicators.

I claim:

1. Apparatus for detecting and correcting anomalies in the equilibrium in the human body including a means (8) for indicating the horizontality of a mobile mechanism mounted on at least one deformable member (5) and on which the user is placed, characterized in that said apparatus comprises a single mobile plate (6) which rests via at least three deformable members (5) on a base (1) resting on the ground and which carries the indicator means (8) of the spirit level kind integrally moving with said mobile plate, and in that said mobile plate carries elements for marking the positioning of one or both feet formed of axial lines (BB', CC', DD') in accordance with the axis of the feet, as well as a removable system (18,20) for fixing the foot with respect to a transverse line AA' dividing the weight of the body, in the middle of said plate.

2. Apparatus according to claim 1, characterized in that the removable fixing system is formed by a rigid semiframe (18) cooperating with notches (17) provided on the plate (6) at the ends of the transverse line AA'.

3. Apparatus according to claim 1, characterized in that the removable fixing system is formed of a resilient strip retained by notches (17) provided on the plate (6) at the ends of the transverse line AA'.

4. Apparatus according to claim 1, characterized in that the removable fixing system is formed of a comb (20) cooperating with holes (19) provided along the axial lines CC', DD', and the transverse line (AA').

5. Apparatus according to claim 1, characterized in that the axial marking lines CC' and DD' are parallel to the median line BB' of the plate and are disposed symmetrically and evenly spaced on each side thereof.

6. Apparatus according to claim 1, characterized in that the spirit level (8) is mounted on an adjustment ball joint.

7. Apparatus according to claim 1, characterized in that the mobile plate (6) is provided with a central recess (14) for housing an additional personal weighing machine (15).

* * * * *